United States Patent
Dynys et al.

(10) Patent No.: US 10,501,373 B1
(45) Date of Patent: Dec. 10, 2019

(54) MULTI-PHASE CERAMIC SYSTEM

(71) Applicants: Frederick Dynys, Chagrin Falls, OH (US); Ali Sayir, Bay Village, OH (US)

(72) Inventors: Frederick Dynys, Chagrin Falls, OH (US); Ali Sayir, Bay Village, OH (US)

(73) Assignee: United States of America as Represented by the Administrator of National Aeronautics and Space Administration, Washington, DC (US)

( * ) Notice: Subject to any disclaimer, the term of this patent is extended or adjusted under 35 U.S.C. 154(b) by 171 days.

(21) Appl. No.: 15/363,140

(22) Filed: Nov. 29, 2016

Related U.S. Application Data (63) Continuation of application No. 14/603,732, filed on Jan. 23, 2015, now abandoned.

(60) Provisional application No. 61/931,180, filed on Jan. 24, 2014.

(51) Int. Cl.
| | |
|---|---|
| *C04B 35/10* | (2006.01) |
| *C04B 35/626* | (2006.01) |
| *C04B 35/64* | (2006.01) |
| *A61L 27/42* | (2006.01) |
| *A61L 27/10* | (2006.01) |
| *A61F 2/32* | (2006.01) |
| *A61F 2/34* | (2006.01) |
| *A61F 2/36* | (2006.01) |
| *C04B 35/50* | (2006.01) |
| *A61F 2/30* | (2006.01) |

(52) U.S. Cl.
CPC .......... *C04B 35/10* (2013.01); *A61F 2/30767* (2013.01); *A61F 2/32* (2013.01); *A61F 2/34* (2013.01); *A61F 2/36* (2013.01); *A61L 27/10* (2013.01); *A61L 27/105* (2013.01); *A61L 27/427* (2013.01); *C04B 35/6261* (2013.01); *C04B 35/6264* (2013.01); *C04B 35/64* (2013.01); *C04B 2235/3217* (2013.01); *C04B 2235/3222* (2013.01); *C04B 2235/3224* (2013.01); *C04B 2235/604* (2013.01); *C04B 2235/6567* (2013.01)

(58) Field of Classification Search
CPC . C04B 35/10; C04B 35/50; C04B 2235/3217; C04B 2235/3244; C04B 2235/3224; A61F 2/34; A61F 2/36
See application file for complete search history.

(56) References Cited

U.S. PATENT DOCUMENTS

| | | | |
|---|---|---|---|
| 4,237,559 A | 12/1980 | Borom | |
| 4,547,910 A | 10/1985 | Roberts et al. | |
| 5,384,293 A * | 1/1995 | Omori | C04B 35/18 501/128 |
| 5,902,763 A * | 5/1999 | Waku | C04B 35/117 501/127 |
| 6,387,132 B1 | 5/2002 | Deppisch et al. | |
| 6,592,798 B1 * | 7/2003 | Omori | C04B 35/117 117/4 |
| 6,753,284 B2 * | 6/2004 | Yamamoto | C04B 35/117 264/663 |

(Continued)

*Primary Examiner* — Erin Snelting
(74) *Attorney, Agent, or Firm* — Robert H. Earp, III; William M. Johnson (57) ABSTRACT

Systems, methods, and other embodiments associated with multi-phase ceramic composites are described herein. Specifically, a multi-phase ceramic composite having a microstructure having at least one solid-state lubricant phase and at least one wear resistant material phase.

15 Claims, 8 Drawing Sheets

(56) References Cited

U.S. PATENT DOCUMENTS

| | | |
|---|---|---|
| 7,022,173 B2 | 4/2006 | Cummings et al. |
| 2004/0241036 A1 | 12/2004 | Meyer-Lindenberg et al. |
| 2005/0109060 A1 | 5/2005 | Cummings et al. |
| 2005/0136176 A1 | 6/2005 | Rosenflanz et al. |
| 2010/0137972 A1 | 6/2010 | Kuntz et al. |
| 2011/0218630 A1 | 9/2011 | Niess et al. |
| 2013/0006356 A1 | 1/2013 | Cook et al. |

* cited by examiner

| | Pin | Disc | Wear mm/hr | Friction | Comments |
|---|---|---|---|---|---|
| 600 | CoCr | CoCr | $4\times10^{-5}/2\times10^{-7}$ | 0.8/0.4 | Commercial Hip Joint |
| 610 | $Al_2O_3/Gd_2O_3$ | $Al_2O_3/Gd_2O_3$ | $4\times10^{-8}/2\times10^{-7}$ | 0.21 | Eutectic Solidification $Al_2O_3/Gd_2O_3=2$ |
| 620 | $Al_2O_3/ZrO_2$ | $Al_2O_3/Gd_2O_3$ | $1\times10^{-6}$ | 1.3 | Laser Solidification $Al_2O_3/Gd_2O_3=2$ Audible Squeak |
| 630 | $Al_2O_3/Gd_2O_3$ | $Al_2O_3/Gd_2O_3$ | $\sim 8\times10^{-7}$ | 0.025 | Sintered $Al_2O_3/Gd_2O_3=3$ |
| 640 | $Al_2O_3/Gd_2O_3$ | $Al_2O_3/Gd_2O_3$ | $8\times10^{-7}$ | 0.03 | Sintered $Al_2O_3/Gd_2O_3=3.3$ |
| 650 | $Al_2O_3/Gd_2O_3$ | $Al_2O_3/Gd_2O_3$ | $3\times10^{-6}$ | 0.03 | Sintered $Al_2O_3/Gd_2O_3=0.6$ |
| 660 | $Al_2O_3/Gd_2O_3$ | $Al_2O_3/Gd_2O_3$ | $3\times10^{-6}$ | 0.02 | Sintered $Al_2O_3/Gd_2O_3=0.3$ |
| 670 | $Al_2O_3/Y_2O_3$ | $Al_2O_3/Y_2O_3$ | $1\times10^{-6}$ | 0.02 | Sintered $Al_2O_3/Y_2O_3=0.4$ |
| 680 | $Al_2O_3/Y_2O_3$ | $Al_2O_3/Y_2O_3$ | $>1\times10^{-6}$ | 0.48 | Sintered $Al_2O_3/Y_2O_3=1.0$ Audible Squeak |
| 690 | $Al_2O_3/Y_2O_3$ | $Al_2O_3/Y_2O_3$ | $>1\times10^{-4}$ | 0.89 | Sintered $Al_2O_3/Y_2O_3=1.4$ |

MULTI-PHASE CERAMIC SYSTEM

CROSS REFERENCE TO RELATED APPLICATIONS

This application is a Continuation Application claiming the benefit of priority from U.S. patent application Ser. No. 14/603,732, filed on Jan. 23, 2015, pending, which claims priority to U.S. Provisional Patent application Ser. No. 61/931,180, entitled "TRIBOLOGICAL PROPERTIES OF RARE EARTH ALUMINATE COMPOSITES", filed Jan. 24, 2014, each of which is hereby incorporated by reference in its entirety.

ORIGIN OF THE INVENTION

The invention described herein was made by employees of the United States Government and may be manufactured and used by or for the Government for Government purposes without the payment of any royalties thereon or therefore.

BACKGROUND

Tribology is the science of the mechanisms of friction, lubrication, adhesion, and wear of interacting surfaces that are in relative motion. Tribology has a large economic impact, ranging from household, industrial, and space applications to biological systems. Wear and friction consume 6% of the gross national product. U.S. energy loss by friction has been estimated to be $70 billion, annual economic lost by wear is $100 billion dollars. This massive economic driving force plays a large role in the development and design of new materials with favorable friction and wear properties. When lost-labor, down-time, and maintenance cost is considered, the economic impact of wear is greater than $500 billion dollars. Therefore, small improvements in energy efficiency (friction) and durability (wear) is cost effective.

BRIEF DESCRIPTION

This brief description is provided to introduce a selection of concepts in a simplified form that are described below in the detailed description. This brief description is not intended to be an extensive overview of the claimed subject matter, identify key factors or essential features of the claimed subject matter, nor is it intended to be used to limit the scope of the claimed subject matter.

Every year, about one million patients worldwide undergo total hip arthroplasty (THA) surgery or hip replacement. This is considered a successful, safe, and cost-effective medical intervention to restore functionality of the hip joint and to regain pain-free mobility in patients suffering from severe joint disease or trauma. The number of people undergoing primary THA and revision surgery is expected to increase further due to an ageing population, decreasing average age at the first operation, and the limited life span of prostheses.

Decades of basic and clinical experimentation have resulted in a vast array of prosthetic designs and material combinations. Several artificial cup-femoral head material combinations are utilized based on the relative hardness of the material combinations. For example, in a soft-on-hard material combination an ultra-high molecular weight polyethylene acetabular cup combined with stainless steel is combined with a femoral head made of cobalt-chromium molybdenum (Co—Cr—Mo) alloy or ceramic. As an example of a hard-on-hard material combination, both the acetabular cup and the femoral head may be made of the same material, such as Co—Cr—Mo (metal-on-metal, MOM) or ceramic (ceramic-on-ceramic, COC). None of THA designs fully replicate the natural human hip joint, and these material combinations have certain drawbacks.

Metal on polyethylene (MOP) represent the most commonly implanted bearing surfaces, whereas MOM and COC couplings are less frequently used. MOP couplings are problematic in the formation of polyethylene wear particles that can induce periprosthetic inflammatory response and osteolysis with subsequent implant failure. Similarly, elevated serum levels of metallic ions have been found in patients with MOM couplings. Metallic ions are associated with adverse effects such as renal toxicity or chromosomal aberrations. COC couplings are more bio-compatible to the human body than MOM and MOP couplings. COC exhibits less susceptibility to third body wear and scratching of the surface and less biologic response to any debris generated by ceramic wear particles. However, COC couplings exhibit a small finite risk for fracture due to brittleness. Additionally, minor patient population with COC implants experience an annoying squeaking noise. A number of mechanisms have been proposed for squeaking: 1) mismatch between liner and head 2) insufficient lubrication 3) particle debris and 4) stripe wear. Squeaking has made impact on commercial application of COC couples.

Described herein are examples of systems, methods, and other embodiments associated with multi-phase ceramic composite. Multi-phase ceramic composites exhibit wear resistance and low sliding friction coefficient that is applicable to artificial joints. Accordingly, the number of revision operations for patients may be reduced. The wear properties of a multi-phase ceramic composite is superior that of the individual constituents due to a microstructure of the multi-phase ceramic composite containing a hard(wear) phase with a lubricating phase.

Under severe conditions of non-lubrication, the multi-phase ceramic Composite outperformed cobalt-chromium (CoCr) alloys under the same load condition. Specifically, in tests, the multi-phase ceramic composite exhibited a tenfold reduction in friction coefficient, a sixfold reduction in wear, and a significant reduction in wear debris. Thus, multi-phase ceramic composites have superior wear properties. Furthermore, biocompatibility improves arthroplasty life and low friction will aid to mitigate squeaking. Resistance to wear is particularly significant in maintaining proper joint function and preventing the further destruction of bone caused by particulate debris generated as the implant parts move against each other. While specific examples are described herein associated to specific joint(s) (e.g., hips) on humans, it is to be understood that the innovation can be employed in alternative joints (e.g., shoulders, knees) without departing from the spirit and scope of the innovation. Additionally, it is contemplated that the innovation can further be applied to applications in non-humans or animals (e.g., horses, dogs). These additional contemplated aspects are to be considered within the scope of this specification and claims appended hereto.

The following description and drawings set forth certain illustrative aspects and implementations. These are indicative of but a few of the various ways in which one or more aspects may be employed. Other aspects, advantages, or novel features of the disclosure will become apparent from the following detailed description when considered in conjunction with the drawings.

BRIEF DESCRIPTION OF THE DRAWINGS

The accompanying drawings, which are incorporated in and constitute a part of the specification, illustrate various systems, methods, and other embodiments of the disclosure. Illustrated element boundaries (e.g., boxes, groups of boxes, or other shapes) in the figures represent one example of the boundaries. In some examples one element may be designed as multiple elements or multiple elements may be designed as one element. In some examples, an element shown as an internal component of another element may be implemented as an external component and vice versa.

FIG. 6 is a wear couple summary for different composites subjected to a force of ten Newtons.

DETAILED DESCRIPTION

Embodiments or examples illustrated in the drawings are disclosed below using specific language. It will nevertheless be understood that the embodiments or examples are not intended to be limiting. Any alterations and modifications in the disclosed embodiments and any further applications of the principles disclosed in this document are contemplated as would normally occur to one of ordinary skill in the pertinent art. Described herein are examples of systems, methods, and other embodiments associated with multi-phase ceramic composites. The rare earth oxides consists of the 15 lanthanide elements along with $Y_2O_3$ and $Sc_2O_3$. They exhibit similar phase formation behavior with $Al_2O_3$. The composition may be altered using rare earth substitution for Yttrium or Gadolinium.

Figure 1A:
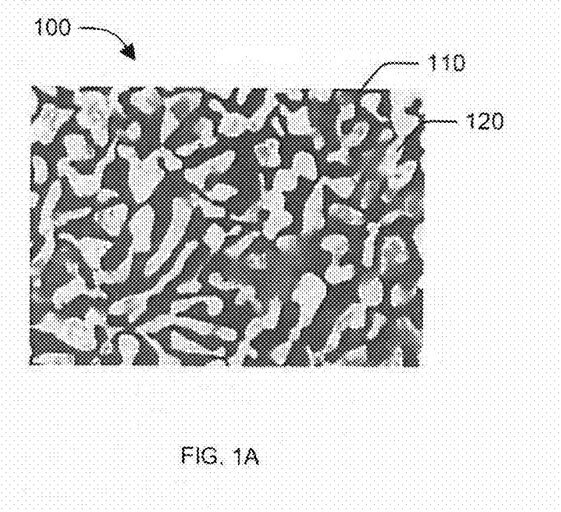
FIG. 1A illustrates one embodiment of a multi-phase ceramic composite.

FIG. 1A illustrates one embodiment of a multi-phase ceramic composite 100.

Specifically, in the embodiment illustrated in the electron micrograph of FIG. 1, the multi-phase ceramic composite 100 is an $Al_2O_3$—$GdAlO_3$ microstructure. In this embodiment, the $Al_2O_3$—$GdAlO_3$ microstructure may be fabricated using directional solidification from the melt produced in-situ composite. The $Al_2O_3$—$GdAlO_3$ microstructure is a dual phase ceramic composite 100 having continuous networks of two phases including a dark phase 110 and a light phase 120. The dark phase 110 is a solid-state lubricant, $GdAl_2O$. The light phase 120 is a wear resistant material, $Al_2O_3$. The continuous networks of the dark phase 110 and the light phase 120 may be randomly interspersed. Alternatively, the continuous networks of the dark phase 110 and the light phase 120 may be arranged in a pattern.

Figure 1B:
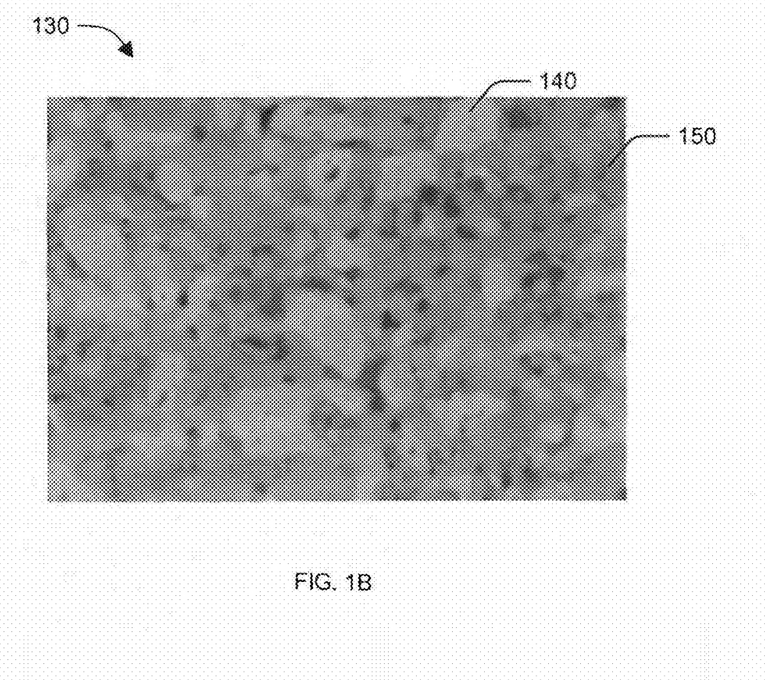
FIG. 1B illustrates another embodiment of a multi-phase ceramic composite.

FIG. 1B illustrates another embodiment of a multi-phase ceramic composite 130 densified by solid state sintering. Specifically, the embodiment is illustrated as electron micrograph. The multi-phase ceramic composite 130 has a molar ratio of $Al_2O_3/Gd_2O_3$ of O.6. Powders of $Al_2O_3$ and $Gd_2O_3$ were mixed by wet milling in ethanol. Mixed powder was dried, and green rods were fabricated by isostatic pressing the powder. Green rods were reactive sintered at 1450° C. for 4 hours in air.

The $Al_2O_3$—$Gd_2O_3$ microstructure is a multi-phase ceramic composite 130 with a phase content (wt. %) 30.74% $Al_2O_3$, 24.1% $Gd_2O_3$, 26.74% $GdAlO_3$ and 18.4% $Gd_4Al_2O_9$. The $Al_2O_3$—$GdAlO_3$ microstructure 130 is a dual phase ceramic composite 100 having continuous networks of two phases including a dark phase 140 and a light phase 150. The dark phase is $Gd_2O_3$. The light phase 140 is $Al_2O_3$. The dark phase 150 is $GdAlO_3$ and/or $Gd_4Al_2O_9$. The distribution of the phases are randomly interspersed. Specimens of the multi-phase ceramic composite 100 may be cut from a sintered rod.

Tribological properties of the multi-phase ceramic composite 100 can be measured under a severe environment and compared to tribological properties of commercial CoCr alloy hip prosthesis. The tribological properties of the multi-phase ceramic composite 100 were found to be superior to CoCr alloy. As discussed above, under the severe conditions of non-lubrication, the multi-phase ceramic composite 100 outperformed the CoCr alloy under the same load condition.

While two phases have been described, the multi-phase ceramic composite 100 may include a greater number of phases. Moreover, the materials used to form the composite may be different based on the desired wear properties. For example, as discussed above, other rare earth oxides may exhibit similar phase formation behavior with $Al_2O_3$. Accordingly, these other rare earth oxides may be used in multi-phase ceramic composites.

A quantitative analysis of the plurality of phases can be conducted using x-ray diffraction. In one embodiment, the x-ray diffraction data is analyzed using the Rietveld method. The method is based on a least-squares fit between step-scan data of a measured diffraction pattern and a simulated X-ray-diffraction (XRD) pattern. The simulated XRD pattern is calculated from based, at least in part, on crystal-structure parameters of each component phase. The simulated XRD pattern may also be calculated based on a scale factor for each constituent phase to adjust the relative intensities of the reflections, parameters describing the peak profile and the background, parameters simulating the instrumental aberrations as well as effects resulting: from size-related strain, preferred orientation, and particle size. The phase abundances of the constituent phases may be directly calculated from the Rietveld model. Therefore, quantitative analysis can be performed without the need of experiments utilizing standard samples for calibration.

The table below shows the phase content of example multi-phase ceramic compositions reactively sintered at 1450° C. for 4 hrs in air.

| Al$_2$O$_3$/Gd$_2$O$_3$ Molar Ratio | Al$_2$O$_3$ wt % | GdAlO$_3$ wt % | Gd$_4$Al$_2$O$_4$ wt % | Gd$_2$O$_3$ wt % |
|---|---|---|---|---|
| 3.3 | 39.04 | 60.96 | 0 | 0 |
| 0.6 | 30.74 | 26.74 | 18.40 | 24.10 |
| 0.3 | 0 | 21.57 | 32.76 | 45.66 |

Figure 2A:
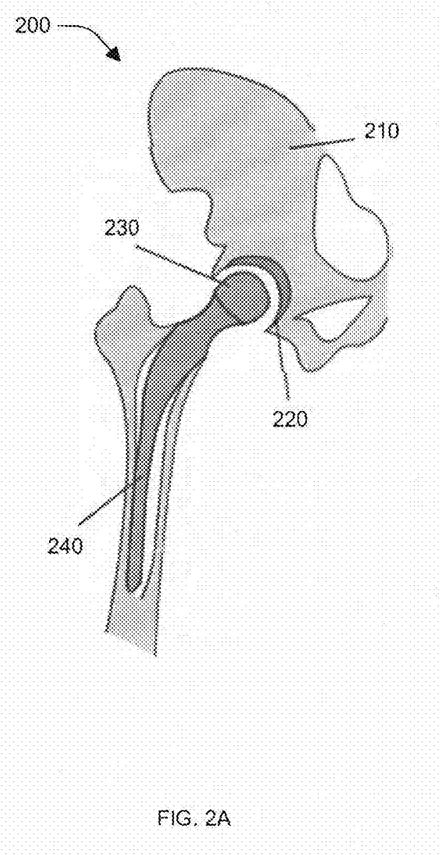
FIG. 2A illustrates a diagram of one embodiment of a multi-phase ceramic composite for use in total hip replacement.

FIG. 2A illustrates a diagram of one embodiment of a multi-phase ceramic composite for use in total hip replacement 200. The hip includes the pelvis 210 having an artificial acetabular cup 220. Specifically, the acetabular cup 220 is anchored in the pelvis 210. The artificial acetabular cup 220 is composed of a shell in which a liner is inserted that provides the load bearing articulating surface. The femoral head 230 moves within the artificial acetabular cup 220. The femoral head 230 is anchored in the femur by a stem 240. This modular design allows the use of different materials that are suitable for the application.

The defective hip joint is replaced with the artificial acetabular cup 220, the femoral head 230, and the stem 240, which replace the damaged natural articulating surfaces. The movement of the femoral head 230 in the artificial acetabular cup 220 is aided by the low friction so that the femoral head 230 and artificial acetabular cup 220 can withstand wear and oscillating mechanical load. Accordingly, a multi-phase ceramic composite may be used on the surface of the acetabular cup 220 and the surface of the femoral head 230 such that the friction between the surface of the acetabular cup 220 and the surface of the femoral head 230 is reduced and the hip joint is able to withstand wear.

Figure 2B:
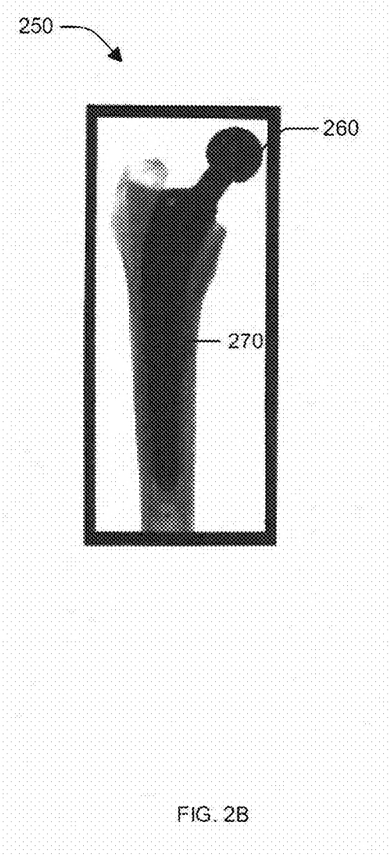
FIG. 2B illustrates an x-ray image of one embodiment of a multi-phase ceramic composite for use in a total hip replacement.

FIG. 2B illustrates an x-ray image of one embodiment of a multi-phase ceramic composite for use in a total hip replacement 250. Specifically, the femoral head 260 and a stem 270. Because the stem 270 provides bone integration. Titanium alloys are however not hard enough for low-friction wear-resistant acetabular cup (not shown) and femoral surfaces. Therefore, other materials are utilized to meet the requirements for the articulating interface between the femoral head 260 and acetabular cup. While the example in FIGS. 2A and 2B is related to total hip replacement, multi-phase ceramic compositions may be utilized in other joints, prosthesis, as well as other high friction and wear applications, such as drilling.

Figure 3:
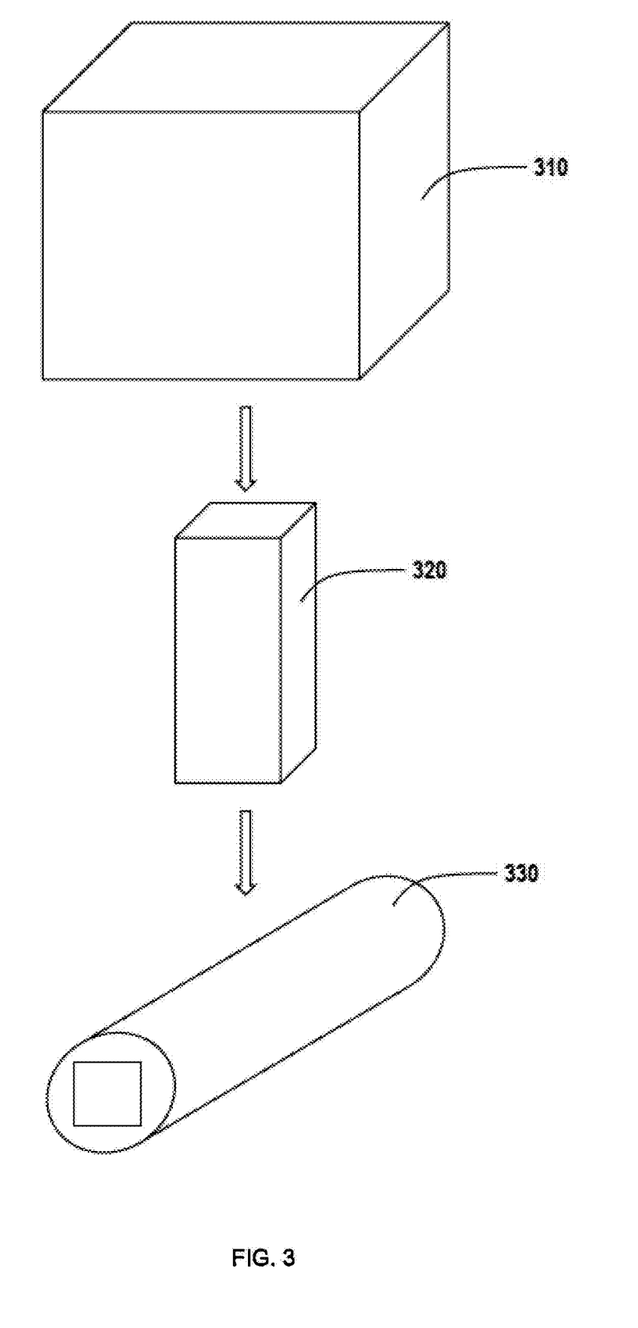
FIG. 3 illustrates one embodiment example of a wear specimen for wear testing associated with multi-phase ceramic composites.

FIG. 3 illustrates one embodiment example of a wear specimen for wear testing associated with multi-phase ceramic composites. The multi-phase ceramic material may be fabricated as a blocks of substrate 310. A pin 320 can be cut from the block of substrate 310. For example, the pin may have the dimensions of 3 millimeters by 3 millimeters by 10 millimeters. The pin 320 may then be set in epoxy as the wear specimen 330.

Figure 4A:
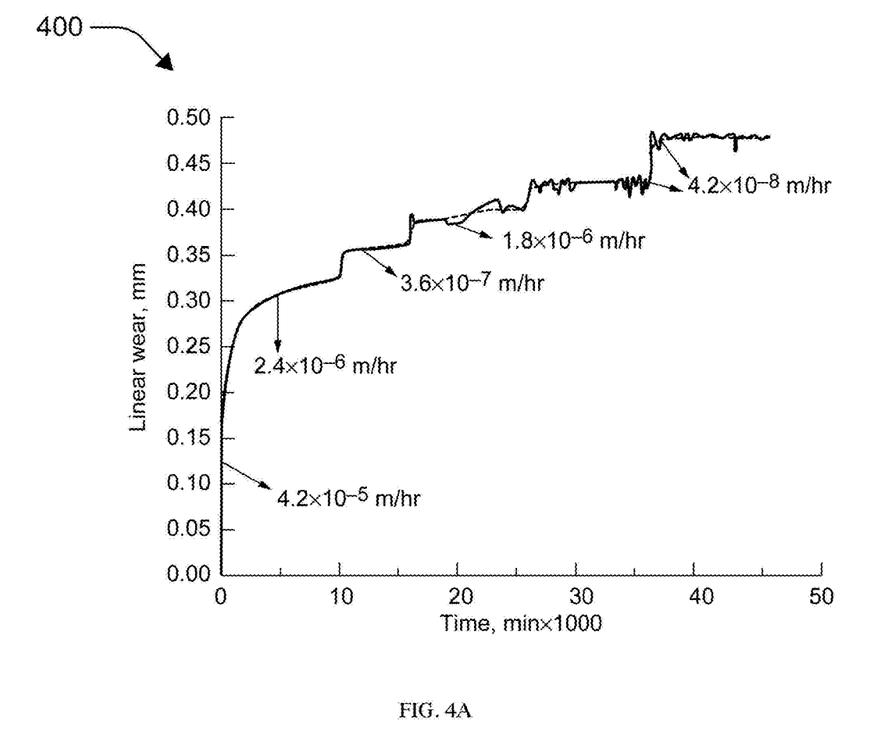
FIG. 4A is a graph illustrating the wear behavior, measured in millimeters of a cobalt chromium alloy over time.

FIG. 4A is a graph 400 illustrating the wear, measured in millimeters of a cobalt chromium (CoCr) alloy over time. The graph 400 illustrates the results of wear experimentation on a cobalt chromium alloy couple. In one embodiment, wear testing may be performed using a wear machine, where CoCr pin and block, are described above with respect to FIG. 3. A linear oscillatory motion may be used for testing. The linear wear of the pin and friction coefficient was measured continuously during the experiments. The coefficient of friction is defined as the ratio between the measured lateral force to the applied normal force. In one embodiment, the wear may be measured at weekly intervals.

The linear wear of the CoCr alloy was measured over 768 hours of testing. The linear wear rate progressively decreased with time. During the first week of testing, the CoCr alloy exhibited the highest wear rates of $4.2 \times 10^{-5}$ m/hr to $2.4 \times 10^{-6}$ m/hr. As illustrated in graph 400, after 416 hours of testing a steady state wear rate of $42 \times 10^{-8}$ m/hr was observed. The initial transitory period can be attributed to the original surface roughness of the bodies in contact and disappeared rapidly as the wear process modified the surface in contact.

Figure 4B:
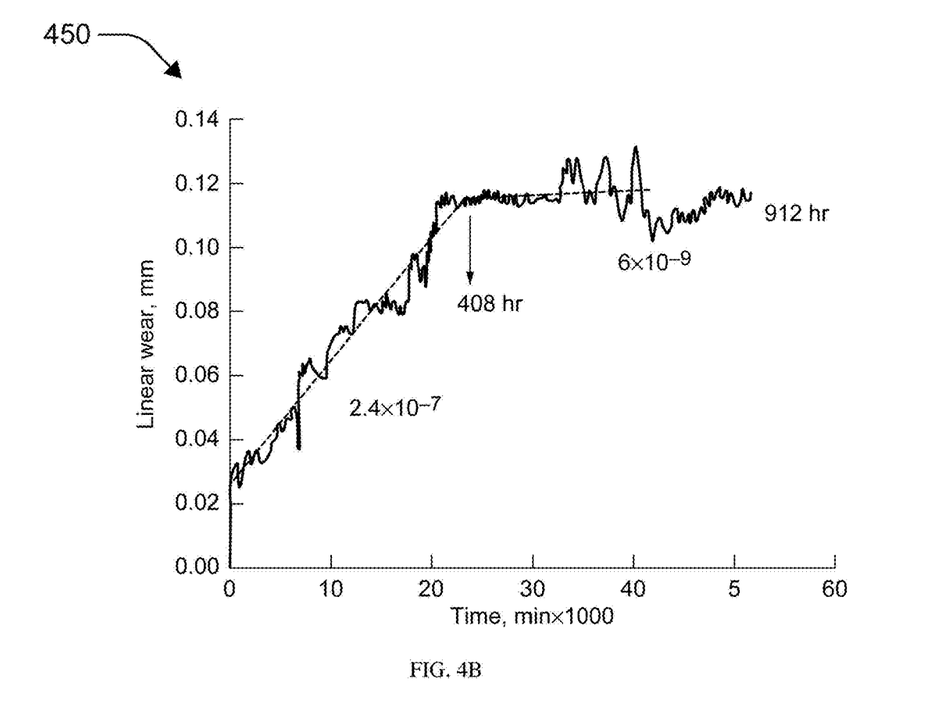
FIG. 4B is a graph illustrating the wear behavior, measured in millimeters of a eutectic solidified $Al_2O_3$—$GdAlO_3$ composite over time.

FIG. 4B is a graph 450 illustrating the wear of a multi-phase ceramic composite. Specifically, the graph 450 illustrates wear measured in millimeters of Al$_2$O$_3$—GdAlO$_3$ over time. As discussed above, the wear was measured at weekly intervals unless the machine stopped due to software issues. The linear wear of the Al$_2$O$_3$-GdAlO$_3$ after 912 hours of wear experimentation is illustrated. Unlike the wear of the CoCr alloy, illustrated in graph 400, there is no aggressive wear at the start of testing. Linear wear rate was steady $2.4 \times 10^{-7}$ m/hr until 408 hours. After 408 hours, the linear wear decreased by a factor of forty and the wear rate changed to $6.0 \times 10^{-9}$ m/hr. Comparing the final linear wear rates of CoCr alloy, shown in graph 400 of FIG. 4A, wear rate is seven times higher than Al$_2$O$_3$—GdAlO$_3$, shown in graph 450 of FIG. 4B.

Figure 5:
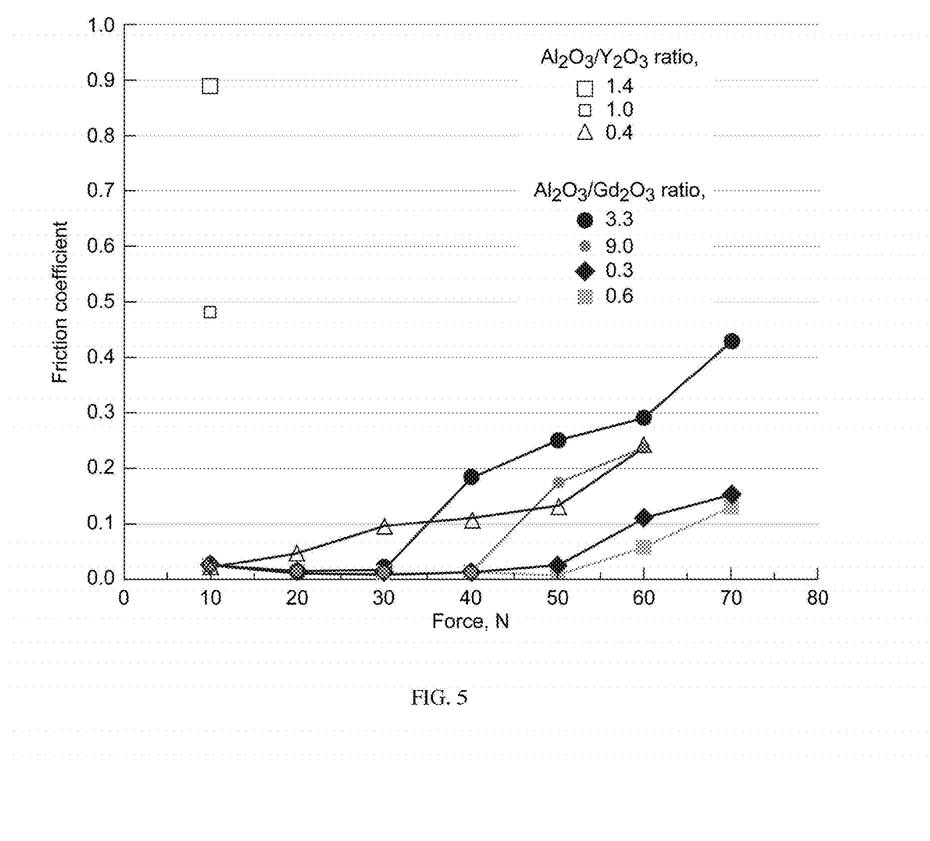
FIG. 5 is a graph illustrating the friction coefficient of composite material as a function of the force exerted on the composite compositions containing $Gd_2O_3$—$Al_2O_3$ and $Y_2O_3$—$Al_2O_3$.

FIG. 5 is a graph illustrating the friction coefficient of composite material as a function of the force exerted on the composite material. The friction coefficient is measured as a function of time. The friction coefficient exhibits dependency upon load, friction increased with load ranging from 0.02 to 0.5. The friction coefficient is 50% lower than CoCr alloy at load of 10 newtons.

FIG. 6, which includes rows 600, 610, 620, 630, 640, 650, 660, 670, 680, 690, is a wear couple summary for different composites subjected to a force of ten newtons. While Al$_2$O$_3$—GdAlO$_3$ has been given as an example of a multi-phase ceramic composite, other composites may also be used. Row 600 is a summary of the wear and friction coefficient of typical composite material CoCr. However, the multi-phase ceramic composites discussed herein are shown to have less wear and lower coefficients of friction. For example, pin and disc combination of Al$_2$O$_3$—Gd$_2$O$_3$ at row 610 showed less wear and demonstrated a lower coefficient of friction. Likewise, pin and disc combination Al$_2$O$_3$—Y$_2$O$_3$ at row 670 showed less wear and demonstrated a lower coefficient of friction.

Figure 7A:
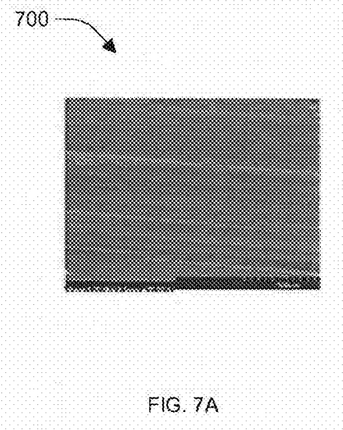
FIG. 7A illustrates wear scarring of a CoCr alloy substrate after wear testing.

FIG. 7A illustrates wear scarring of a CoCr alloy substrate after wear testing. Specifically, the wear scarring 700 on the substrate of the CoCr alloy occurred after 768 hours of testing. Wear grooves are observed. Definitive scarring 700 is approximately 0.45 mm in depth. The small particles removed by wear cause groove formation. Accordingly, a large amount of particle debris was generated. Particles are harder than the metal, abrasively wearing the surface.

Figure 7B:
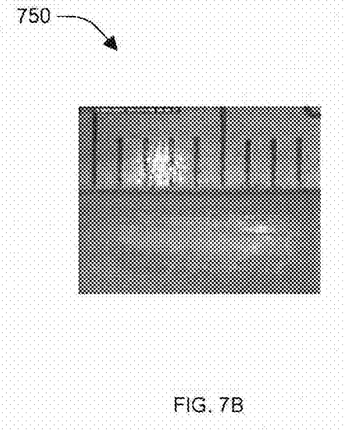
FIG. 7B illustrates wear scarring of one embodiment of a multi-phase ceramic composite after wear testing.

FIG. 7B illustrates wear scarring 750 of one embodiment of a multi-phase ceramic composite after wear testing. FIG. 7B shows the scarring after 912 hours of testing. Wear depth is about is about 0.1 mm, ¼ of depth observed for CoCr alloy. Accordingly, the scarring 750 of the multi-phase ceramic composite is considerably less than the scarring 700 illustrated in FIG. 7A.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

While for purposes of simplicity of explanation, illustrated methodologies are shown and described as a series of blocks. The methodologies are not limited by the order of the blocks as some blocks can occur in different orders and/or concurrently with other blocks from that shown and described. Moreover, less than all the illustrated blocks may be used to implement an example methodology. Blocks may be combined or separated into multiple components. Furthermore, additional and/or alternative methodologies can employ additional, not illustrated blocks. The methods described herein is limited to statutory subject matter under 35 U.S.C § 101.

To the extent that the term "includes" or "including" is employed in the detailed description or the claims, it is intended to be inclusive in a manner similar to the term "comprising" as that term is interpreted when employed as a transitional word in a claim.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the disclosure is not limited to the specific details, the representative apparatus, and illustrative examples shown and described. Thus, this application is intended to embrace alterations, modifications, and variations that fall within the scope of the appended claims, which satisfy the statutory subject matter requirements of 35 U.S.C. § 101.

Various operations of embodiments are provided herein. The order in which one or more or all of the operations are described should not be construed as to imply that these operations are necessarily order dependent. Alternative ordering will be appreciated based on this description. Further, not all operations may necessarily be present in each embodiment provided herein.

As used in this application, "or" is intended to mean an inclusive "or" rather than an exclusive "or". Further, an inclusive "or" may include any combination thereof (e.g., A, B, or any combination thereof). In addition, "a" and "an" as used in this application are generally construed to mean "one or more" unless specified otherwise or clear from context to be directed to a singular form. Additionally, at least one of A and B and/or the like generally means A or B or both A and B. Further, to the extent that "includes", "having", "has", "with", or variants thereof are used in either the detailed description or the claims, such terms are intended to be inclusive in a manner similar to the term "comprising".

Further, unless specified otherwise, "first", "second", or the like are not intended to imply a temporal aspect, a spatial aspect, an ordering, etc. Rather, such terms are merely used as identifiers, names, etc. for features, elements, items, etc. For example, a first channel and a second channel generally correspond to channel A and channel B or two different or two identical channels or the same channel.

Although the disclosure has been shown and described with respect to one or more implementations, equivalent alterations and modifications will occur based on a reading and understanding of this specification and the annexed drawings. The disclosure includes all such modifications and alterations and is limited only by the scope of the following claims.

The invention claimed is:

1. A method for making a multi-phase ceramic composite, the method comprising;
   providing a rare earth metal powder;
   providing an $Al_2O_3$ powder;
   mixing the rare earth metal powder first powder and the $Al_2O_3$ powder to form a mixed powder;
   drying the mixed powder;
   isostatically pressing the mixed powder to form a green component; and
   sintering the green component to form a sintered component;
   wherein the sintered component includes continuous networks of two phases, namely, a solid-state lubricant phase comprising gadolinium and a wear resistant phase comprising $Al_2O_3$, and wherein the two phases are randomly interspersed, wherein a molar ratio of the wear resistant phase to the solid state lubricant phase is between 0.3 and 2.0, wherein an entirety of the sintered component is constructed from constituents of the rare earth metal and $Al_2O_3$ powders.

2. The method of claim 1, wherein the solid-state lubricant phase comprises $Gd_4Al_2O_9$ or $Gd_2O_3$.

3. The method of claim 1, wherein the mixing step is performed by wet milling the $Al_2O_3$ powder and the rare earth metal powder in ethanol.

4. The method of claim 3, wherein the sintering step is performed at 1450 degrees C. for 4 hours in air.

5. The method of claim 1, wherein the multi-phase ceramic composite comprises the solid-state lubricant phase, the wear resistant phase, and a third phase.

6. The method of claim 1, further comprising using the multi-phase ceramic composite in a joint prosthesis.

7. The method of claim 6, further comprising using the multi-phase ceramic composite on interacting surfaces of an artificial acetabular cup and a femoral head of a hip replacement.

8. The method of claim 1, wherein the molar ratio is less than 1.0.

9. The method of claim 8, wherein the solid state lubricant phase does not include aluminum.

10. A method for making a multi-phase ceramic composite, the method comprising;
    providing a $Gd_2O_3$ powder;
    providing an $Al_2O_3$ powder;
    mixing the $Gd_2O_3$ powder and the $Al_2O_3$ powder to form a mixed powder;
    drying the mixed powder;
    isostatically pressing the mixed powder to form a green component; and
    sintering the green component to form a sintered component;
    wherein the sintered component includes continuous networks of two phases, namely, a solid-state lubricant phase comprising $Gd_2O_3$ and a wear resistant phase comprising $Al_2O_3$, wherein the two phases are randomly interspersed throughout the multi-phase ceramic composite, wherein a molar ratio of the wear resistant phase to the solid state lubricant phase is between 0.3 and 2.0, wherein an entirety of the sintered component is constructed from constituents of the $Gd_2O_3$ powder and the $Al_2O_3$ powder.

11. The method of claim 10, wherein the mixing step is performed by wet milling the $Al_2O_3$ powder and the $Gd_2O_3$ powder in ethanol.

12. The method of claim 11, wherein the sintering step is performed at 1450 degrees C. for 4 hours in air.

13. The method of claim 10, wherein the multi-phase ceramic composite comprises the at least one solid-state lubricant phase, the at least one wear resistant phase, and a third phase.

14. The method of claim 10, further comprising using the multi-phase ceramic composite in a joint prosthesis.

15. The method of claim 14, further comprising using the multi-phase ceramic composite on interacting surfaces of an artificial acetabular cup and a femoral head of a hip replacement.

\* \* \* \* \*